(12) United States Patent
Chen et al.

(10) Patent No.: US 11,266,670 B2
(45) Date of Patent: Mar. 8, 2022

(54) USE OF SCUTELLARIN IN A MEDICAMENT AND A MODULATOR FOR PREVENTING OR TREATING DISEASES, MEDICAMENT, AND MODULATOR

(71) Applicant: University of Macau, Taipa (CN)

(72) Inventors: Xin Chen, Taipa (CN); Ruixin Li, Taipa (CN); Shaokui Chen, Taipa (CN)

(73) Assignee: University of Macau, Macau (CN)

( * ) Notice: Subject to any disclaimer, the term of this patent is extended or adjusted under 35 U.S.C. 154(b) by 0 days.

(21) Appl. No.: 16/422,134

(22) Filed: May 24, 2019

(65) Prior Publication Data
US 2020/0281957 A1    Sep. 10, 2020

(30) Foreign Application Priority Data
Mar. 5, 2019   (CN) .......................... 201910165076.2

(51) Int. Cl.
*A61K 31/7048*   (2006.01)
*A61P 35/00*   (2006.01)

(52) U.S. Cl.
CPC .......... *A61K 31/7048* (2013.01); *A61P 35/00* (2018.01)

(58) Field of Classification Search
CPC . A61K 31/7048; A61K 31/366; A61K 31/381
See application file for complete search history.

(56) References Cited

U.S. PATENT DOCUMENTS 8,197,868 B2 *   6/2012   Cohen .................. A61K 36/539
424/741

OTHER PUBLICATIONS

Isela (Journal of Biomedical Science; 2017; 24:90, pp. 1-8).*
Mahmoud (Oncoimmunology; 2012; 1(3): 363-364).*
Martinez (Frontiers in Immunology; 2019, 10, 1942, pp. 1-9).*
Kan (BMC Complementary and Alternative Medicine; 2017, 17:41, pp. 1-10).*

* cited by examiner

*Primary Examiner* — Pancham Bakshi
(74) *Attorney, Agent, or Firm* — Schwegman Lundberg & Woessner, P.A.

(57) ABSTRACT

The present disclosure discloses use of scutellarin in a medicament and a modulator for preventing or treating diseases, a medicament, and a modulator, which is related to the technical field of medicine. The present disclosure discloses use of scutellarin in the preparation of a medicament for preventing or treating a disease caused or mediated by interaction between TNF and TNFR2. The research in the present disclosure has shown that scutellarin is capable of selectively inhibiting TNF-induced death of WEHI-13VAR cells and significantly inhibiting TNF-induced proliferation of Tregs, accompanied with down-regulation of TNFR2 and Foxp3 expression in Tregs. This indicates that scutellarin can be used to treat or prevent relevant diseases caused or mediated by the interaction between TNF and TNFR2, and the present disclosure provides a new idea or means for preventing or treating relevant diseases caused or mediated by the interaction between TNF and TNFR2.

3 Claims, 10 Drawing Sheets

USE OF SCUTELLARIN IN A MEDICAMENT AND A MODULATOR FOR PREVENTING OR TREATING DISEASES, MEDICAMENT, AND MODULATOR

CROSS-REFERENCE TO RELATED APPLICATION

The present disclosure claims priority to Chinese Patent Application No. 2019101650762, filed with the Chinese Patent Office on Mar. 5, 2019, and entitled "Use of Scutellarin in a Medicament and a Modulator for Preventing or Treating Diseases, Medicament, and Modulator", which is incorporated herein by reference in its entirety.

TECHNICAL FIELD

The present disclosure relates to the technical field of medicine, and in particular to use of scutellarin in a medicament and a modulator for preventing or treating diseases, a medicament, and a modulator.

BACKGROUND ART $CD4^+$ $Foxp3^+$ regulatory T cells (Tregs) are essential for maintaining immune homeostasis and are beneficial to the treatment of autoimmune diseases. On the other hand, they also promote tumor growth and help immune evasion to inhibit anti-tumor immune responses. Therefore, it is important to modulate Tregs during the treatment phase to treat some diseases, such as autoimmune diseases, graft versus host diseases and cancer. Therefore, understanding the modulation of Tregs function is a prerequisite for up- or down-regulation of Tregs activity for therapeutic purposes.

Tumor necrosis factor (TNF) is a pleiotropic cytokine that has multiple functions in immunity, inflammation, cell growth regulation, tumorigenesis, autoimmunity, and so on. TNF is activated and acts by binding to tumor necrosis factor receptor I (TNFR1) and tumor necrosis factor receptor II (TNFR2), which are two distinct membrane receptors. Since TNFR2 is expressed at a higher density on naturally occurring Tregs than TNFR1, and TNF is capable of functionally stimulating the expansion of Tregs by TNFR2, the interaction between TNF and TNFR2 is critical for the treatment of diseases.

SUMMARY

An object of the present disclosure is to provide use of scutellarin in preparation of a medicament for preventing or treating a disease.

Another object of the present disclosure is to provide use of scutellarin in preparation of a modulator for modulating proliferation or death of cells.

Another object of the present disclosure is to provide a medicament for preventing or treating a disease.

Another object of the present disclosure is to provide a modulator for modulating proliferation or death of cells.

The present disclosure is implemented as follows.

TNF can activate Tregs via tumor necrosis factor receptor II (TNFR2), which is one of TNF receptors that are preferentially expressed on Tregs. The TNF-TNFR2 interaction plays a crucial and decisive role in Tregs function, and in the case of no expression of TNFR2, Tregs has little or no inhibitory activity. The TNF-TNFR2 interaction has a promoting effect on Tregs proliferation, thus TNFR2 can serve as an important marker or target for activating or inhibiting the activity of Tregs by targeting TNFR2.

The research in the present disclosure has shown that scutellarin is capable of selectively inhibiting TNF-induced death of WEHI-13VAR cells and significantly inhibiting TNF-induced proliferation of Tregs, accompanied with down-regulation of TNFR2 and Foxp3 expression in Tregs. This indicates that scutellarin can be used to treat or prevent relevant diseases caused or mediated by the interaction between TNF and TNFR2, for example, for treating or preventing a disease caused or mediated by proliferation or death of TNFR2-expressing cells induced by the interaction between TNF and TNFR2. The present disclosure provides a new idea or means for preventing or treating relevant diseases caused or mediated by the interaction between TNF and TNFR2.

Based on this, the present disclosure is proposed as follows.

In one aspect, the present disclosure provides use of scutellarin or a pharmaceutically acceptable salt thereof in preparation of a medicament for preventing or treating a disease, wherein the disease is caused or mediated by interaction between TNF and TNFR2.

Further, in some embodiments of the present disclosure, the disease is caused or mediated by proliferation or death of TNFR2-expressing cells induced by the interaction between TNF and TNFR2.

Further, in some embodiments of the present disclosure, the TNFR2-expressing cells are selected from the group consisting of regulatory T lymphocytes, endothelial cells, microglia, nerve cells, cardiomyocytes, oligodendrocytes, myeloid-derived suppressor cells, and mesenchymal stem cells.

Further, in some embodiments of the present disclosure, the scutellarin prevents or treats the disease by blocking the interaction between TNF and TNFR2 to inhibit the proliferation of regulatory T lymphocytes.

Further, in some embodiments of the present disclosure, the disease is selected from the group consisting of cancer, graft versus host diseases, and autoimmune diseases. In addition, other diseases caused by abnormal expression of TNF protein, such as diabetes, atherosclerosis, infectious diseases, degenerative diseases and so on, are also included.

In another aspect, the present disclosure provides use of scutellarin or a pharmaceutically acceptable salt thereof in preparation of a modulator for modulation of proliferation or death of cells, wherein the cells are TNFR2-expressing cells, and the proliferation or death of the cells is caused or mediated by interaction between TNF and TNFR2.

Further, in some embodiments of the present disclosure, the modulation of proliferation or death of cells is inhibition of proliferation or death of cells.

Further, in some embodiments of the present disclosure, the scutellarin performs the inhibition of proliferation or death of cells by blocking the interaction between TNF and TNFR2.

Further, in some embodiments of the present disclosure, the TNFR2-expressing cells are selected from the group consisting of regulatory T lymphocytes, endothelial cells, microglia, nerve cells, cardiomyocytes, oligodendrocytes, myeloid-derived suppressor cells, and mesenchymal stem cells.

In another aspect, the present disclosure provides use of scutellarin or a pharmaceutically acceptable salt thereof as a TNFR2 inhibitor.

In another aspect, the present disclosure provides use of scutellarin or a pharmaceutically acceptable salt thereof as a TNFR2 inhibitor in preparation of a medicament for inhibiting TNFR2.

In another aspect, the present disclosure provides use of scutellarin or a pharmaceutically acceptable salt thereof as a TNFR2 inhibitor in preparation of a medicament for inhibiting interaction between TNF and TNFR2.

In another aspect, the present disclosure provides use of scutellarin or a pharmaceutically acceptable salt thereof in preparation of a medicament for preventing or treating a disease associated with activation of regulatory T lymphocytes, wherein the scutellarin or a pharmaceutically acceptable salt thereof prevents or treats the disease associated with activation of regulatory T lymphocytes by inhibition of TNFR2.

In another aspect, the present disclosure provides a medicament for preventing or treating a disease, wherein the disease is caused by interaction between TNF and TNFR2, and the medicament comprises scutellarin or a pharmaceutically acceptable salt thereof as an active ingredient and at least one pharmaceutically acceptable excipient.

In another aspect, the present disclosure provides a modulator for modulating proliferation or death of cells, wherein the modulator comprises scutellarin or a pharmaceutically acceptable salt thereof, the cells are TNFR2-expressing cells, and the proliferation or death of the cells is caused or mediated by interaction between TNF and TNFR2.

BRIEF DESCRIPTION OF DRAWINGS

In order to more clearly illustrate the technical solutions of the embodiments of the present disclosure, drawings required to be used in the embodiments will be described briefly below. It should be understood that the following drawings only illustrate some of the embodiments of the present disclosure and shall not be considered as limiting the scope of the present disclosure. For a person skilled in the art, other relevant drawings may be obtained according to these drawings without inventive effort.

DETAILED DESCRIPTION OF EMBODIMENTS

In order to make the objects, technical solutions and advantages of the embodiments of the present disclosure clearer, the technical solutions of the embodiments of the present disclosure will be described clearly and completely below. Examples are carried out in accordance with the conventional conditions or the conditions recommended by the manufacturer, if specific conditions are not indicated. All reagents or instruments used, whose manufacturers are not indicated, are commercially available conventional products.

The features and characteristics of the present disclosure are described in further detail below in connection with Examples.

Example 1

TNF Induces Death of WEHI-13VAR Cells Via TNFR2.

Figure 1:
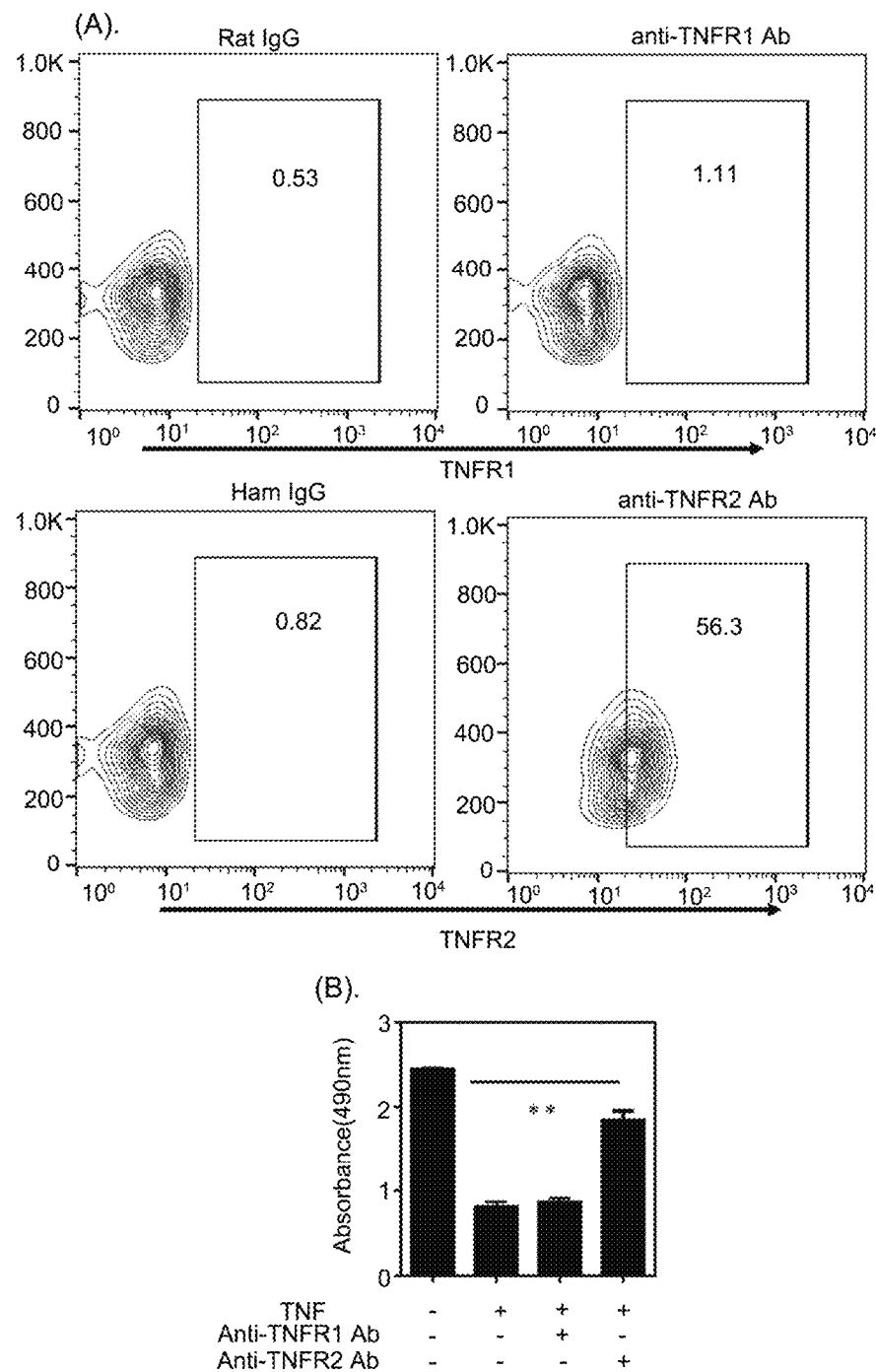
FIG. 1. TNF induces death of WEHI-13VAR cells via TNFR2. (A) Expression of TNFR1 and TNFR2 on surfaces of WEHI-13VAR cells. Cells were harvested after incubation for 24 hours and further labeled with PE-TNFR1 antibody or PE-TNFR2 antibody or their isotype controls, respectively. The surface expression of TNFR1 or TNFR2 on WEHI-13VAR cells was analyzed by flow cytometry. (B) TNF-induced death of WEHI-13VAR cells is mediated by TNFR2. The WEHI-13VAR cells were treated with TNF in the presence or absence of anti-TNFR1 antibody or anti-TNFR2 antibody. The control group was treated only with medium. The anti-TNFR2 antibody significantly blocked TNF-induced cell death, whereas the anti-TNFR1 antibody had no effect.  $p<0.01$, *$p<0.001$.

WEHI-13VAR is a fibrosarcoma cell line that is extremely sensitive to TNF-induced cell death in the presence of AcD (0.5 µg/ml) and is commonly used in TNF bioassays. In TNF bioassays, the presence of AcD is a standard approach designed to increase the sensitivity of cells to TNF. TNF acts by binding to its two functionally distinct receptors, TNFR1 and TNFR2. To identify which TNF receptor was expressed on WEHI-13VAR cells, we measured the expression of TNFR1 and TNFR2 on WEHI-13VAR by FACS. The results showed that WEHI-13VAR cells expressed higher levels of TNFR2. In the case of labeling with PE anti-mouse TNFR2 antibody, the expression of TNFR2 was higher than in the case of labeling with the isotype control by 50%. However, the results of labeling with PE anti-mouse TNFR1 indicated that TNFR1 was minimally expressed on the cells (FIG. 1A). Furthermore, in order to investigate which TNF receptor is responsible for TNF-induced cell death, we stimulated the cells with TNF, and co-cultured the cells with anti-TNFR1 antibody or anti-TNFR2 antibody for 24 hours. Cell viability was measured by MTT. The results show that TNFR2, rather than TNFR1, is responsible for TNF-induced cell death, and the cytotoxicity of TNF to WEHI-13VAR is significantly eliminated by blockage of TNFR2 (FIG. 1B). Therefore, it is hypothesized that TNF-induced death of WEHI-13VAR cells is mediated by TNFR2, rather than TNFR1. Thus, the WEHI-13VAR cell line and TNF can be used as a stable system for screening for potent compounds that are capable of inhibiting TNF-induced cell death via the TNFR2 or TNFR2 signaling pathway.

Example 2

DZXX Specifically Inhibits TNF-Induced Death of WEHI-13VAR Cells.

Figure 2:
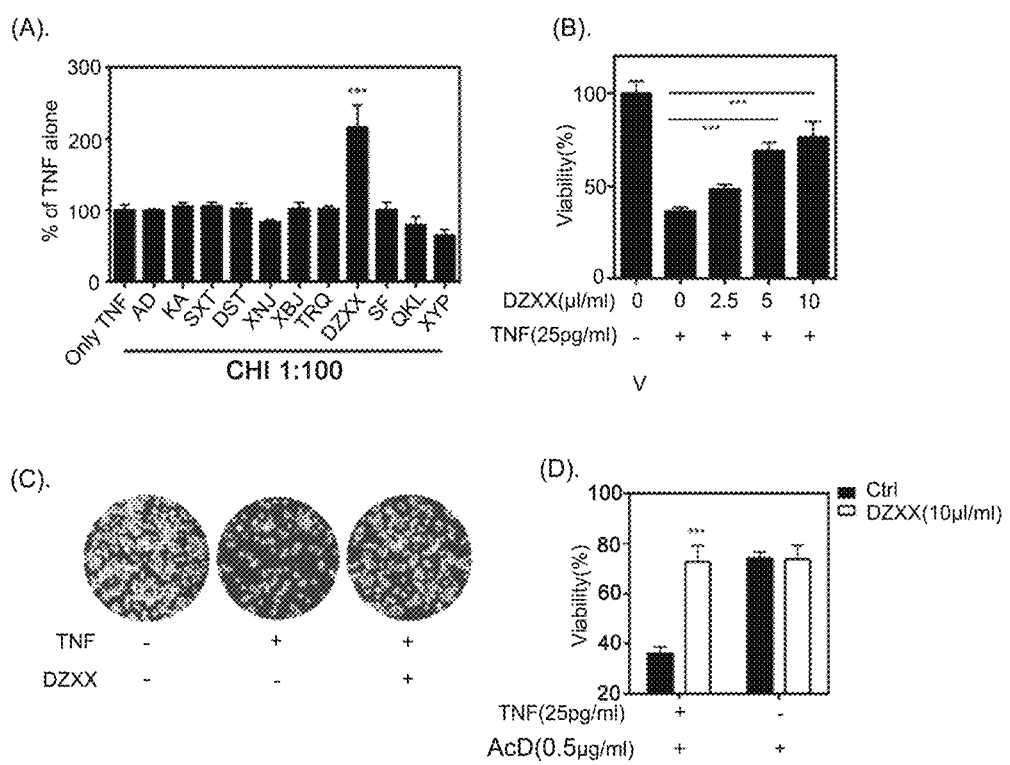
FIG. 2. DZXX specifically inhibits TNF-induced death of WEHI-13VAR cells. (A) Eleven different Chinese herb injections (CHIs, 10 µl/ml) were screened by using WEHI-13VAR cells in the presence of TNF (25 pg/ml) and actinomycin D(AcD) (0.5 µg/ml), and the cells were pretreated with CHIs for 1 hour before stimulated with TNF. After co-incubation for 24 hours, the cell viability of the TNF plus CHIs group was compared with the TNF alone group. Compared with other CHIs, DZXX has a strong inhibitory effect on TNF-induced death of WEHI-13VAR cells. (B) WEHI-13VAR cells were treated with DZXX at different concentrations (2.5-10 µl/ml) in the presence of TNF (25 pg/mL) and AcD, and the control group was treated with medium. After 24 hours, the cell viability of the administration group was compared with the control group. (C) Images of WEHI-13VAR cells show the number of cells in the control group and administration group. The administration group was treated with TNF (25 pg/ml) or TNF plus DZXX (10 µl/ml). (D) Comparison of TNF (25 pg/ml) plus AcD (0.5 µg/ml) group and AcD alone group, in the presence or absence of DZXX (10 µl/ml) and co-cultured for 24 hours. ***$p<0.001$. The data as shown represent at least three separate experiments with similar results (N=3, mean±SEM).

CHIs are injections developed in China and approved by the China Food and Drug Administration. They consist of several specific compounds and have passed safety assessment. We screened eleven CHIs and assessed their effects on WEHI-13VAR cells by TNF bioassay. The cells were pre-treated with CHIs (10 µl/ml) for 1 hour, and then the cells were stimulated with murine recombinant TNF (25 pg/ml). After co-culture for 24 hours, the viability of the cells co-treated with CHIs and TNF was compared to the TNF group. The results showed that DZXX (We named DengZhanXiXin Chinese medicine injection as DZXX, the main component of which was scutellarin) significantly inhibited the death of WEHI-13VAR cells induced by TNF (25 pg/mL) in the presence of AcD (0.5 µg/ml) (FIG. 2A). Moreover, DZXX (2.5-10 µl/ml) inhibited TNF-induced death of WEHI-13VAR cells in a dose-dependent manner (FIG. 2B). After treatment with 10 µl/ml DZXX, nearly 70% of cell death was inhibited. In addition, when WEHI-13VAR cells were treated with TNF (25 pg/ml) in the presence or absence of DZXX (10 µl/ml), it was found by microscopic observation that WEHI-13VAR is very sensitive to TNF, while DZXX has significantly inhibitory effect on TNF-induced cell death (FIG. 2C). In addition, AcD is also cytotoxic, which may induce death of approximately 30% of WEHI-13VAR cells (FIG. 2D). However, DZXX only specifically inhibits TNF-induced death of WEHI-13VAR cells, rather than AcD-induced cell death.

Example 3

DZXX Inhibits TNF-Induced Proliferation of Tregs and TNFR2 Expression In Vitro.

Figure 3:
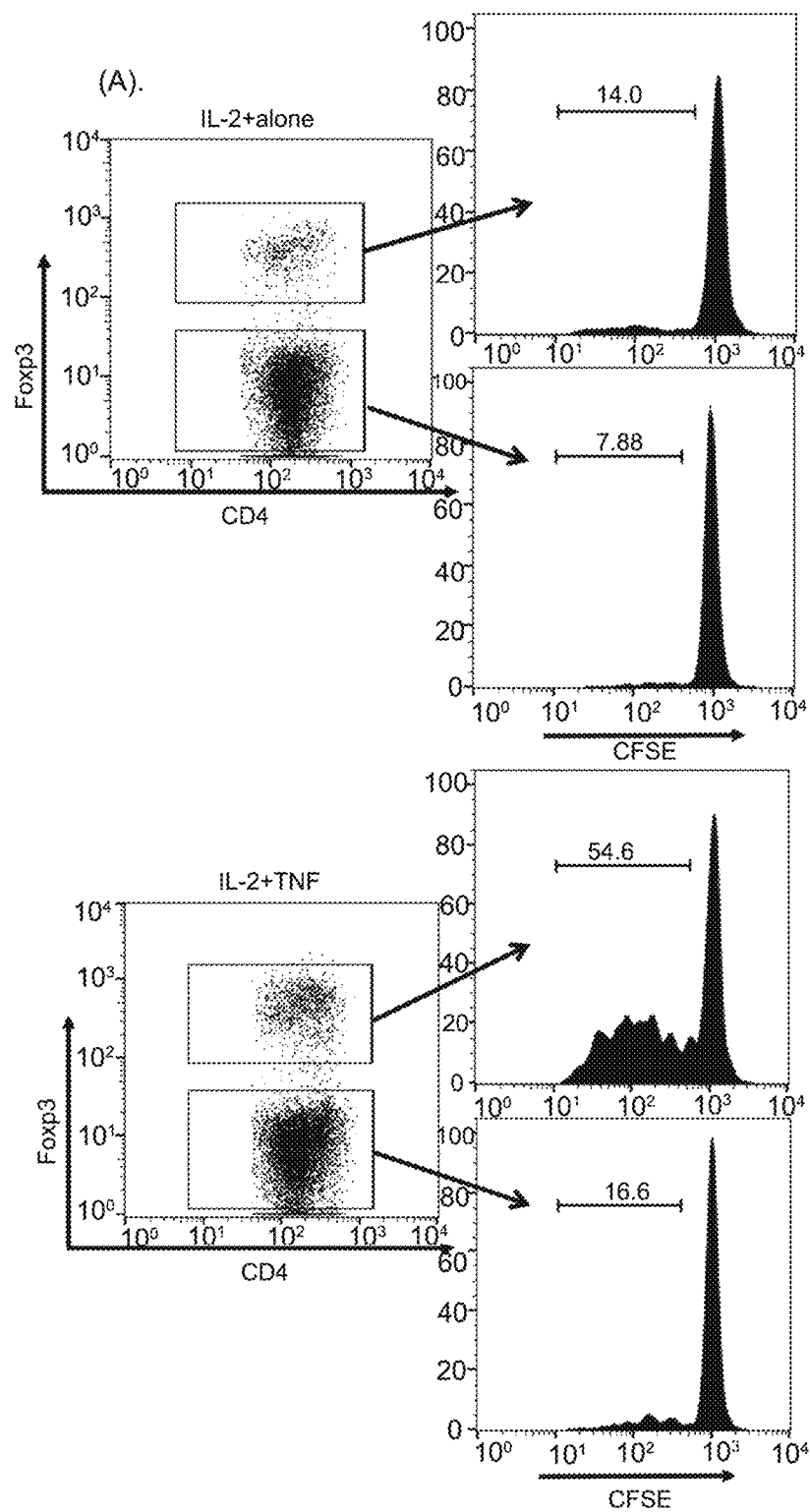
FIG. 3. DZXX inhibits TNF-induced expansion of Tregs and up-regulation of TNFR2 expression on Tregs in vitro. CD4$^+$ T cells were purified from lymph nodes and spleens of normal C57BL/6J mice by MACS. The cells were labeled with CFSE and cultured with medium alone or with DZXX (20 µl/ml) in the presence of IL-2 (10 ng/mL) or IL-2+TNF (10 ng/mL each). After 72 hours, the proliferation of Tregs and the proportion of Foxp3$^+$ cells were analyzed by FACS based on CFSE expression and Foxp3 expression. (A) TNF preferentially stimulated the proliferation of Tregs in the presence of IL-2. (B) DZXX blocked TNF-mediated proliferation of Tregs. (C) DZXX blocked TNF-mediated proliferation percentage of Tregs. (D) DZXX reduced Foxp3 expression on Tregs in cultured CD4$^+$ T cells. (E) Typical FACS plots of the proportion of TNFR2$^+$ cells in Tregs. (F) Summary of the proportion of TNFR2$^+$ cells in CD4$^+$Foxp3$^+$ Tregs. (G) Summary of mean fluorescence intensity (MFI) of TNFR2 expression on Tregs (by gating on Foxp3$^+$ cells) (N=3, mean±SEM).  $p<0.01$, * $p<0.001$, compared to the "TNF+IL-2" group. The data as shown are representative of at least three separate experiments with similar results.
Figure 3:
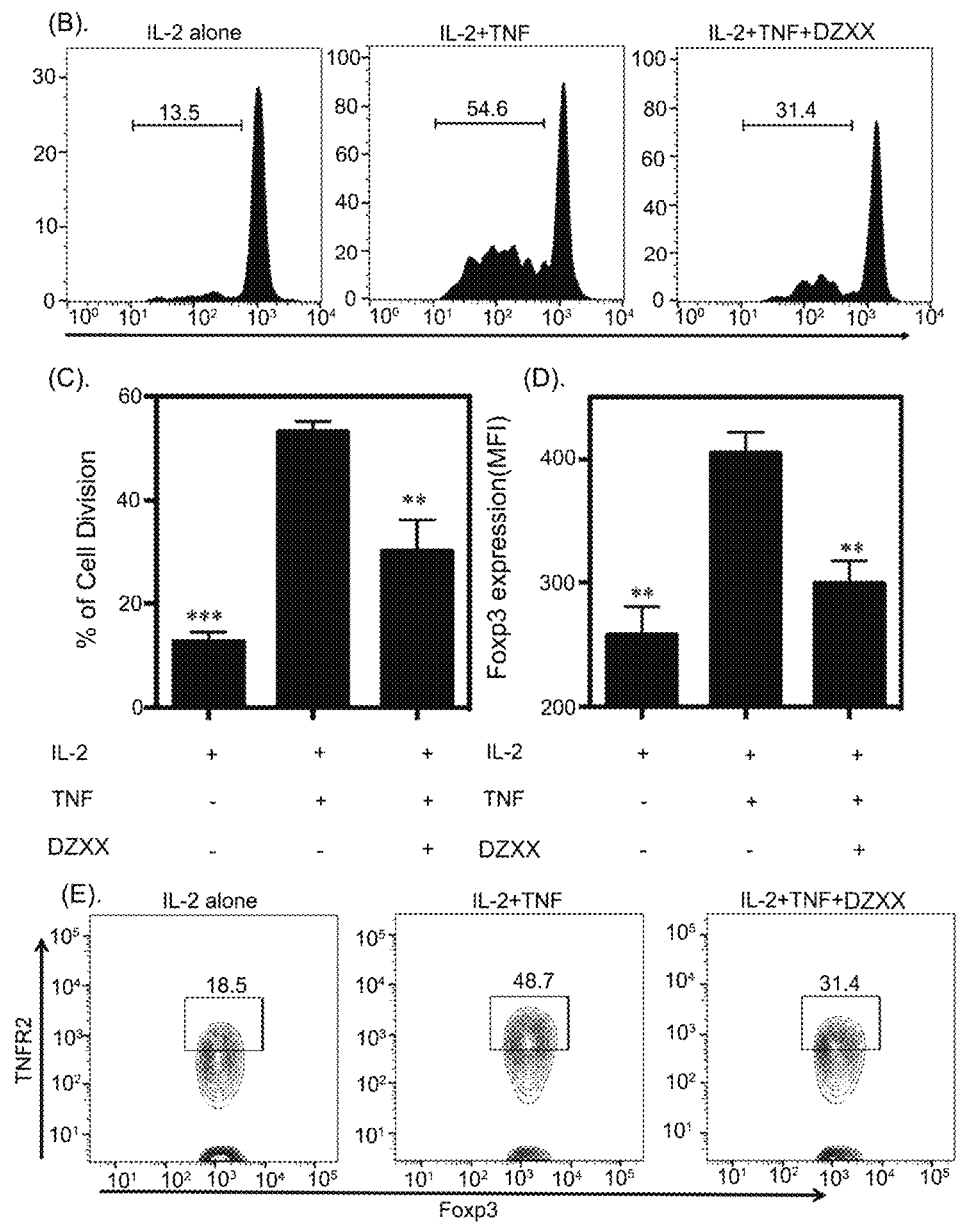
Figure 3:
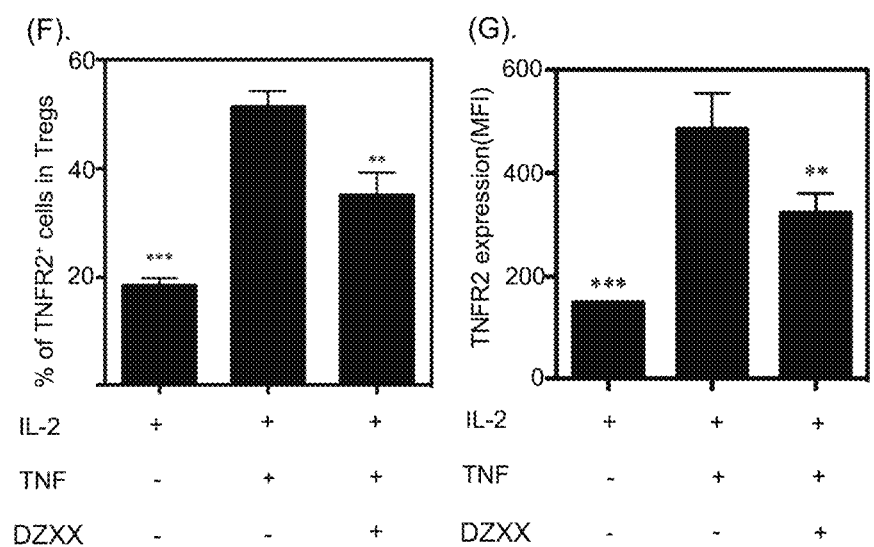
Figure 7:
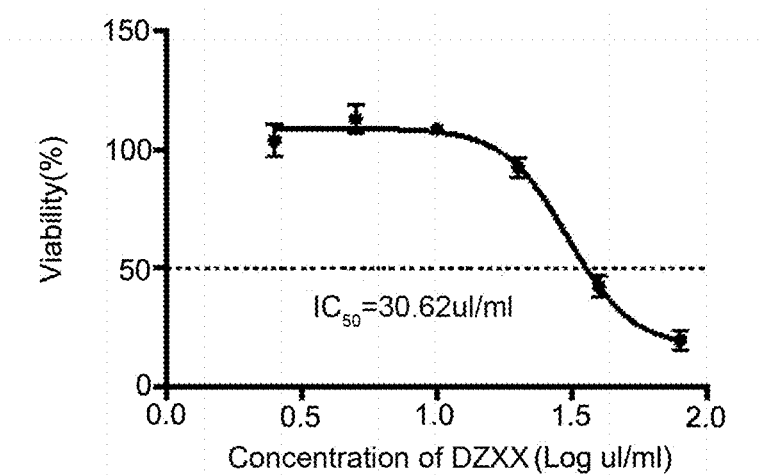
FIG. 7 shows 50% inhibitory concentration (IC50) of lymphocytes with DZXX in vitro. Lymphocytes were obtained from lymph nodes of normal C57BL/6J mice, and the lymphocytes were co-cultured with different concentrations of DZXX (0-80 µl/ml) in vitro in the presence of IL-2 (10 ng/mL), respectively. After 3 days, the activity of the lymphocytes was measured using 3-(4,5-Dimethylthiazol-2-yl)-2,5-diphenyltetrazolium bromide (MTT). The IC50 of lymphocytes with DZXX in vitro was 30.62 µl/ml.

We examined the effect of DZXX on TNF-induced proliferation of Tregs in an in vitro experiment. CD4$^+$ T cells from spleens and lymph nodes of normal mice were isolated by MACS. IL-2 was used to culture cells to maintain their survival. TNF preferentially stimulated the proliferation of Tregs, resulting in replication and proliferation of more than 50% of Tregs (FIG. 3A). As shown in FIGS. 3B-D, 20 µl/ml of DZXX inhibited TNF-induced proliferation of Tregs at an inhibition rate of 30% ($p<0.01$). The Foxp3 expression MFI per cell in the cultured CD4$^+$ T cells was also significantly reduced by the treatment with DZXX, at an inhibition rate of 26.1% (FIG. 3D, $p<0.01$). The concentration of DZXX used in in vitro studies was higher than IC50 (FIG. 7). The level of surface expression of TNFR2 is associated with the immunosuppressive function of Tregs. TNF preferentially stimulates and upregulates the expression of TNFR2 on Tregs. As shown in FIGS. 3E-G, the expression of TNFR2 on Tregs after treatment with TNF was up-regulated more than 2-fold compared to culture with IL-2 alone. DZXX inhibits TNF-induced up-regulation of TNFR2±Tregs and TNFR2 expression. Thus, DZXX can inhibit TNF-induced expression of TNFR2 on Tregs.

Example 4

Scutellarin Specifically Inhibits TNF-Induced Death of WEHI-13VAR Cells.

Figure 4:
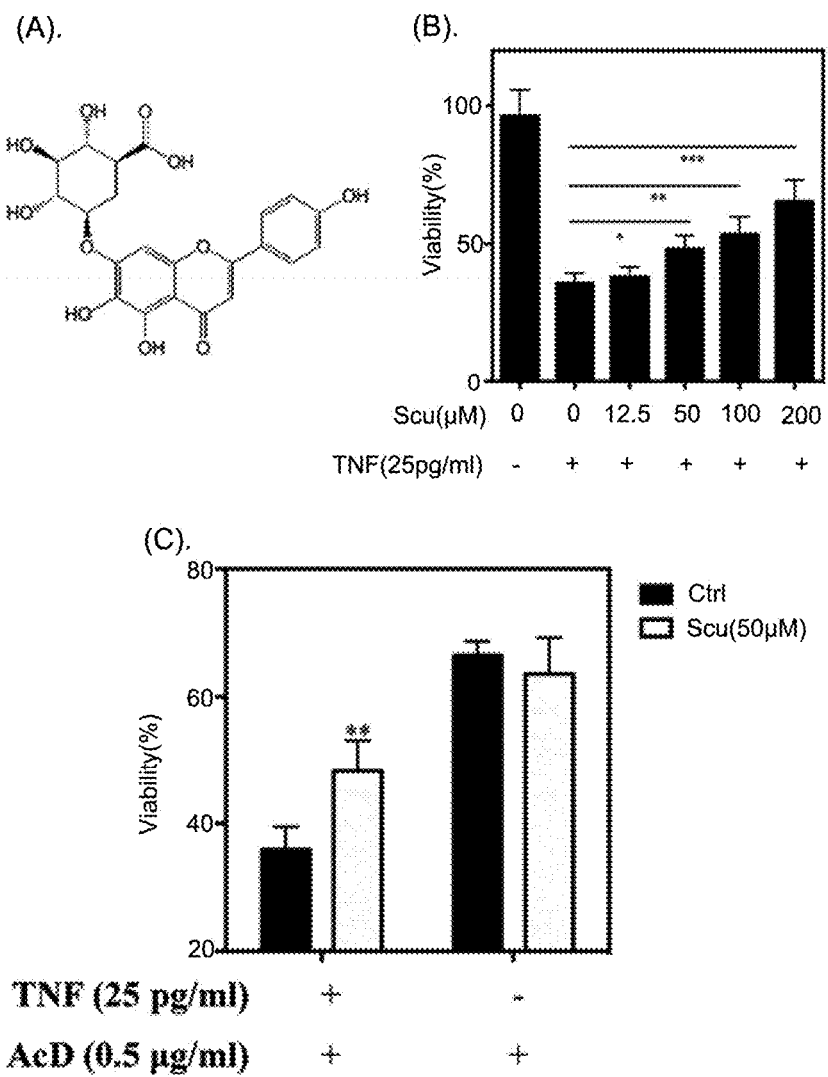
FIG. 4. Scutellarin, the main compound in DZXX, specifically inhibits TNF-induced death of WEHI-13VAR cells. (A) The chemical structure of scutellarin is shown. (B) WEHI-13VAR cells were treated with scutellarin in a concentration range (12.5-200 µM) in the presence of TNF (25 pg/mL) and AcD, and the control group was treated with medium. After 24 hours, the cell viability of the treatment group was compared with the control group. (C) Comparison of TNF (25 pg/ml) plus AcD (0.5 µg/ml) group and AcD alone treatment group, in the presence or absence of scutellarin (50 µM). *** $p<0.001$. The data as shown represent at least three separate experiments with similar results (N=3, mean±SEM).

Scutellarin is a flavonoid compound isolated from *Erigeron breviscapine*, which is the main component of DZXX officially listed in the Chinese Pharmacopoeia (FIG. 4A). To investigate the effect of scutellarin on WEHI-13VAR cells, the cells were treated with gradiently varying concentrations (12.5-200 µM) of scutellarin. As previously reported, scutellarin significantly inhibited TNF-induced death of WEHI-13VAR cells (FIG. 4B). Within this concentration range, scutellarin had no significant cytotoxicity against WEHI-13VAR cells. Moreover, scutellarin did not inhibit AcD-induced cell death compared to the TNF-stimulated group (FIG. 4C). In this case, we can conclude that scutellarin specifically inhibits TNF-induced cell death.

Example 5

Scutellarin Inhibits TNF-Induced Up-Regulation of Tregs and TNFR2 Expression In Vitro.

Figure 5:
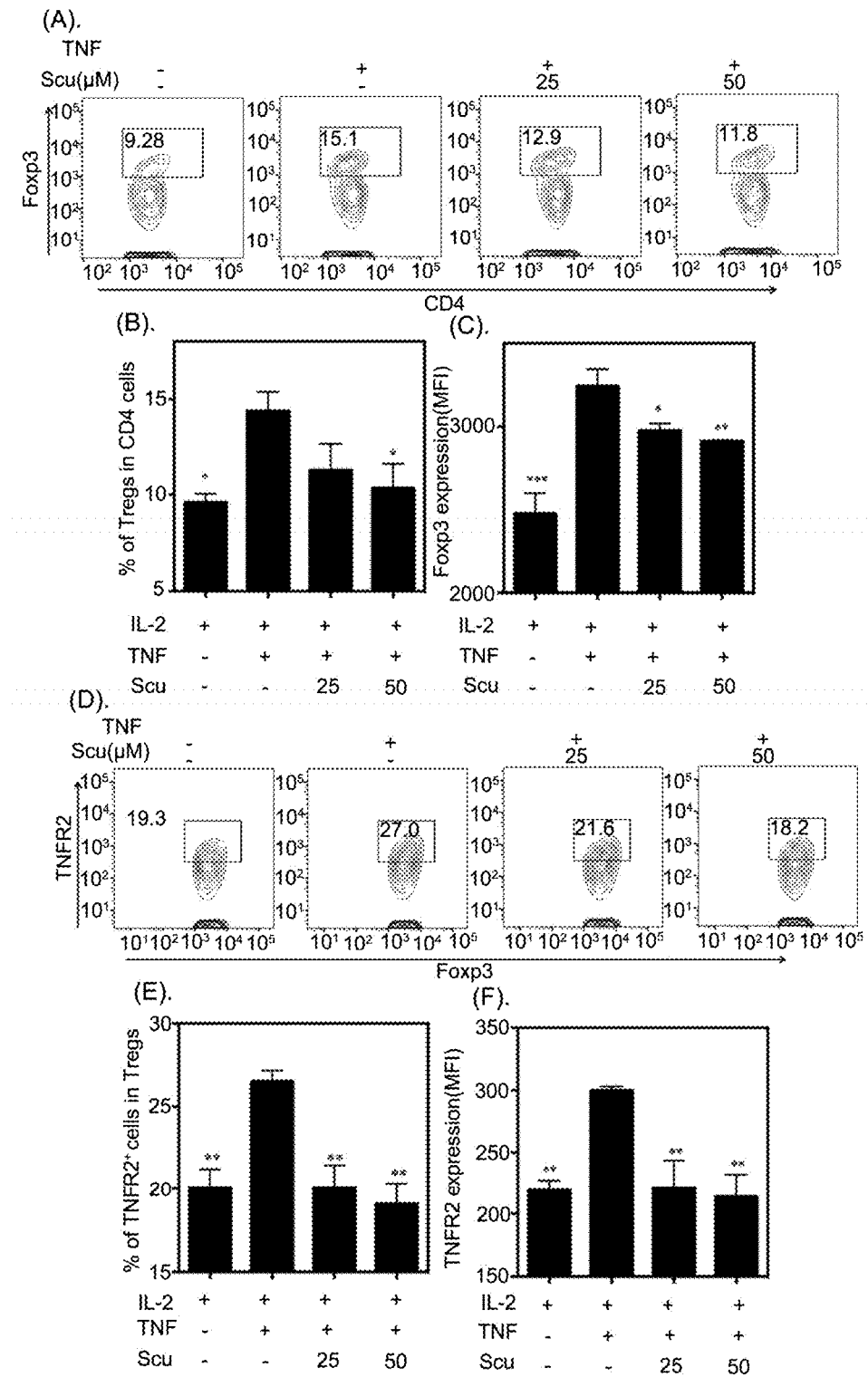
FIG. 5. Scutellarin inhibits TNF-induced expansion of Tregs and up-regulated TNFR2 expression on Tregs in vitro. Lymphocytes were cultured in the presence of IL-2 (10 ng/mL) or IL-2+TNF (10 ng/mL each), with medium alone or with scutellarin (25-50 µM) for 72 hours. (A) Typical FACS analysis of Tregs is shown. The data as shown are representative of at least three separate experiments with similar results. The numbers in the FACS plots show the proportion of cells in the respective quadrants. (B) Summary of the proportion of CD4$^+$Foxp3$^+$ cells in CD4$^+$ cells. (C) Summary of MFI of Foxp3 expression on Tregs. (D) Typical FACS plots of the proportion of TNFR2$^+$ cells in Tregs. (E) Summary of the proportion of TNFR2$^+$ cells in CD4$^+$Foxp3$^+$ Tregs. (F) Summary of MFI of TNFR2 expression on Tregs (by gating on Foxp3$^+$ cells) (N=3, mean±SEM).  $p<0.01$, * $p<0.001$, compared to the "TNF+IL-2" group. The data as shown are representative of at least three separate experiments with similar results.

We then explored the effect of scutellarin on the TNF-induced proliferation of Tregs in an in vitro experiment. Therefore, lymph nodes of C57BL/6J mice were harvested, and lymphocytes were cultured with IL-2 to maintain cell survival. Two different concentrations of scutellarin (25 or 50 µM) were administered to an administration group. In the presence of TNF, Tregs proliferated approximately 2-fold (FIG. 5A). As shown in FIGS. 5A-B, scutellarin at 50 µM significantly inhibited TNF-induced proliferation of Tregs ($p<0.05$). Moreover, scutellarin dose-dependently inhibited the increase in Foxp3 expression MFI on each cell treated with TNF (FIG. 5C, $p<0.05$ to 0.001). In this in vitro study, the concentration of scutellarin was not significantly cytotoxic, with the 50% lethal dose of scutellarin being higher than 100 µM. Furthermore, TNF up-regulated the expression of TNFR2 on Tregs as compared to culture with IL-2 alone. However, scutellarin dose-dependently inhibited TNF-induced up-regulation of TNFR2±Tregs and expression of TNFR2 (FIGS. 5D-F, $p<0.01$). Therefore, scutellarin can inhibit the proportion of TNFR2±Tregs and the expression of TNFR2 on Tregs treated with TNF.

Example 6

Scutellarin Inhibits LPS-Induced In Vivo Expansion of Tregs in Mice.

Figure 6:
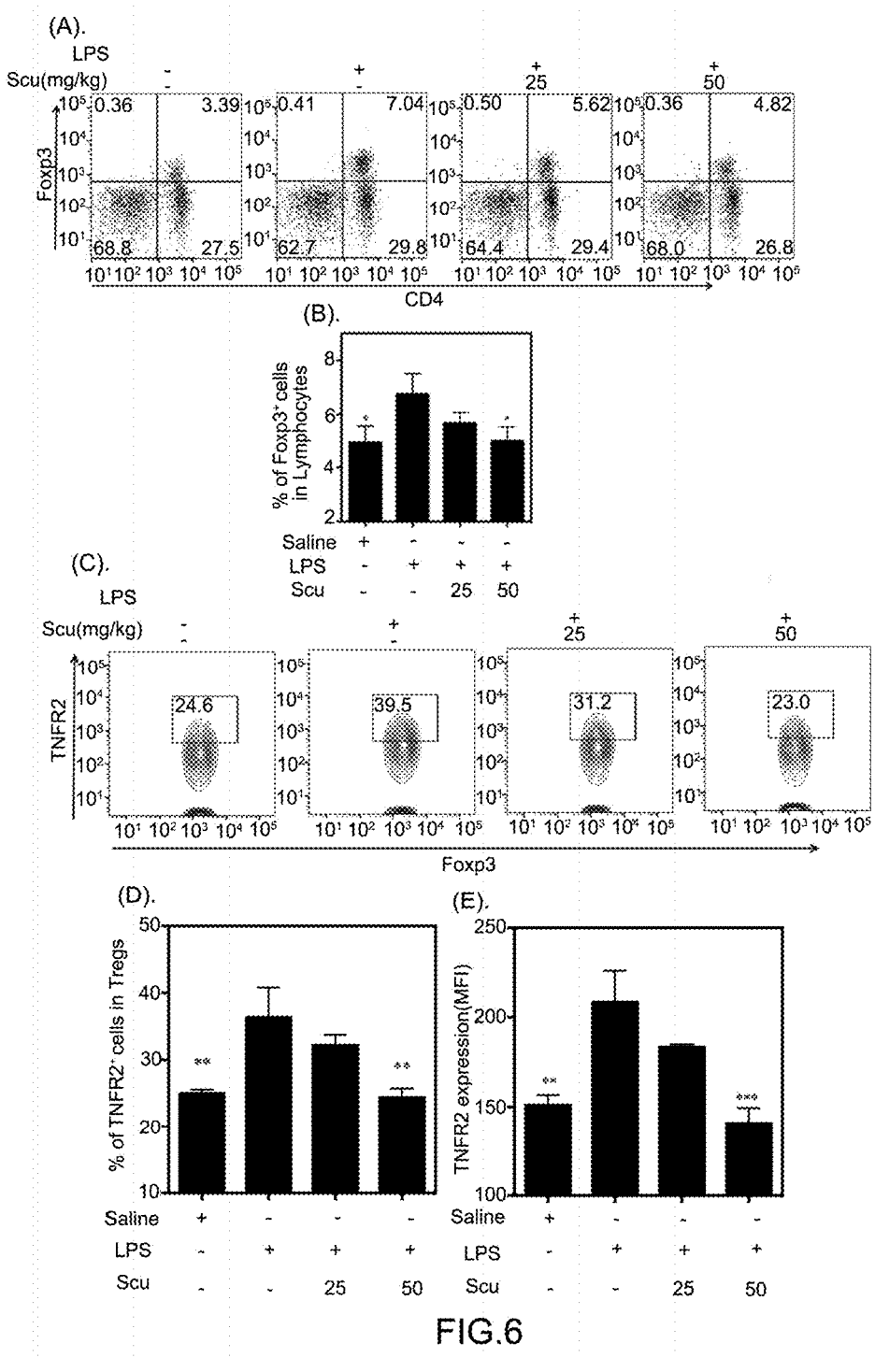
FIG. 6. Scutellarin inhibits the expansion of Tregs in lipopolysaccharide (LPS)-treated mice. C57BL/6J mice were injected with 200 µg of LPS (i.p.) or saline, and treated with or without scutellarin (25 or 50 mg/kg/d) immediately after LPS stimulation. The scutellarin was dissolved in saline. All mice were sacrificed after 24 hours after LPS treatment, and spleens and lymph nodes were collected. The proportion of Foxp3 in lymphocytes and expression of TNFR2 on Tregs were analyzed by FACS, gating on Foxp3+ cells. (A) Proportion of Tregs in lymphocytes. The numbers show the proportion of gated cells. Typical FACS plots are shown. (B) Summary of the proportion of Foxp3+ cells. The numbers show the proportion of positive cells in the respective quadrants. (C) Proportion of TNFR2+ cells in Tregs. Typical FACS plots are shown. (D) Summary of the proportion of TNFR2+ cells in CD4+Foxp3+Tregs. (E) Summarized data on MFI of TNFR2 expression in CD4+Foxp3+ subsets. * $p<0.05$,  $p<0.01$, * $p<0.001$, compared to the LPS alone group.

Our previous studies have demonstrated that TNF-TNFR2 interaction is responsible for LPS-induced proliferation of Tregs in mice. This model was used to test whether scutellarin has the ability to inhibit TNF-induced proliferation of Tregs in an in vivo experiment. As shown in FIGS. 6A-B, the proportion of Foxp3$^+$ cells in splenic CD4$^+$ T cells increased from 9.28% to 15.1% ($p<0.05$) after LPS stimulation for 24 hours. Similarly, the proportion of Foxp3$^+$ cells in lymphocytes after LPS stimulation was also increased compared to the control group (FIG. 6B). The expression of TNFR2 on Tregs in lymphocytes was significantly increased (FIGS. 6C-D, $p<0.01$). Immediately after treatment with LPS, scutellarin (50 mg/kg/day) was administered, which completely inhibited LPS-induced proliferation of Tregs (FIGS. 6A-B). In addition, scutellarin completely inhibited LPS-induced up-regulation of TNFR2 expression on Tregs (FIGS. 6C-E). Therefore, scutellarin inhibits TNFR2-mediated activation and proliferation of Tregs in both in vitro and in vivo experiments.

Example 7

Inhibitory Effect of Scutellarin on 4T1 Cells In Vitro

Figure 8:
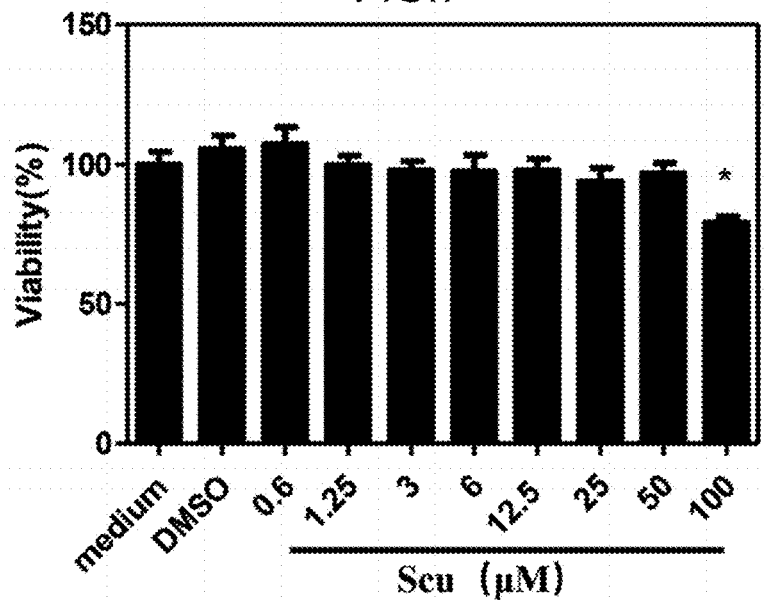
FIG. 8 shows an inhibitory effect of scutellarin on 4T1 cells in vitro. 4T1 cells were co-cultured with scutellarin at different concentrations (0-100 µM) in vitro. After 24 h, the activity of 4T1 cells was measured using MTT. Scutellarin at 100 µM could significantly inhibit the growth of 4T1 cells in vitro.

We explored the inhibitory effect of scutellarin on 4T1 cells in vitro, respectively. 4T1 cells were co-cultured with scutellarin at different concentrations (0-100 µM) in vitro. After 24 h, the activity of 4T1 cells was measured using MTT. The viability of cells treated with scutellarin was compared to the medium group. The results showed that scutellarin at 100 µM could significantly inhibit the growth of 4T1 cells (FIG. 8).

Example 8

In Vitro Reduction of Expression of TNFR2 on 4T1 Cells by Scutellarin

Figure 9:
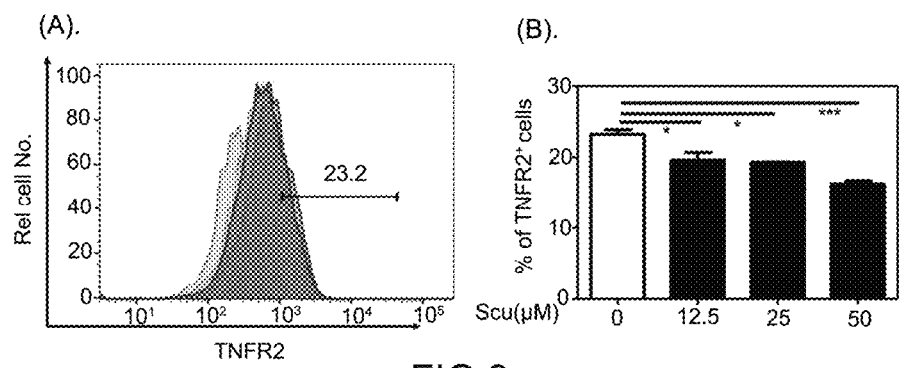
FIG. 9 shows in vitro reduction of the expression of TNFR2 on 4T1 cells by scutellarin. 4T1 cells were co-cultured with scutellarin at different concentrations (0-50 µM) in vitro, respectively. After 24 h, the expression of TNFR2 on 4T1 cells was measured using flow cytometry. In vitro, scutellarin at each of 12.5, 25, and 50 µM could significantly inhibit the expression of TNFR2 on 4T1 cells. Scutellarin at 50 µM had the best inhibitory effect.

Next, we explored the effect of scutellarin on the expression of TNFR2 on 4T1 cells in vitro. 4T1 cells were co-cultured with scutellarin at different concentrations (0-50 µM) in vitro, respectively. After 24 h, the expression of TNFR2 on 4T1 cells was measured using flow cytometry. The amount of TNFR2 expressed on the cells treated with scutellarin was compared to untreated cells. The results showed that scutellarin at each of 12.5, 25, and 50 µM could significantly inhibit the expression of TNFR2 on 4T1 cells. Scutellarin at 50 µM had the best inhibitory effect (FIG. 9).

Example 9

In Vitro Reduction of Expression of TNFR2 on 4T1 Cells by Scutellarin

Figure 10:
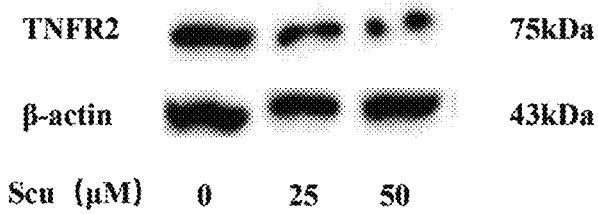
FIG. 10 shows in vitro reduction of the expression of TNFR2 on 4T1 cells by scutellarin. 4T1 cells were co-cultured with scutellarin at different concentrations (0-50 µM) in vitro, respectively. After 24 h, the expression of TNFR2 on 4T1 cells was measured using Western Blotting. Scutellarin at both 25 and 50 µM could significantly inhibit the expression of TNFR2 on 4T1 cells in vitro.

Moreover, we co-cultured 4T1 cells with scutellarin at different concentrations (0-50 µM) in vitro, respectively. After 24 h, the expression of TNFR2 on 4T1 cells was measured using Western Blotting. The amount of TNFR2 expressed on the cells treated with scutellarin was compared to untreated cells. The results showed that scutellarin at both 25 and 50 μM could significantly inhibit the expression of TNFR2 on 4T1 cells in vitro (FIG. 10).

Example 10

Inhibition of Tumor Growth in a Mouse 4T1 Tumor Model by Scutellarin

Figure 11:
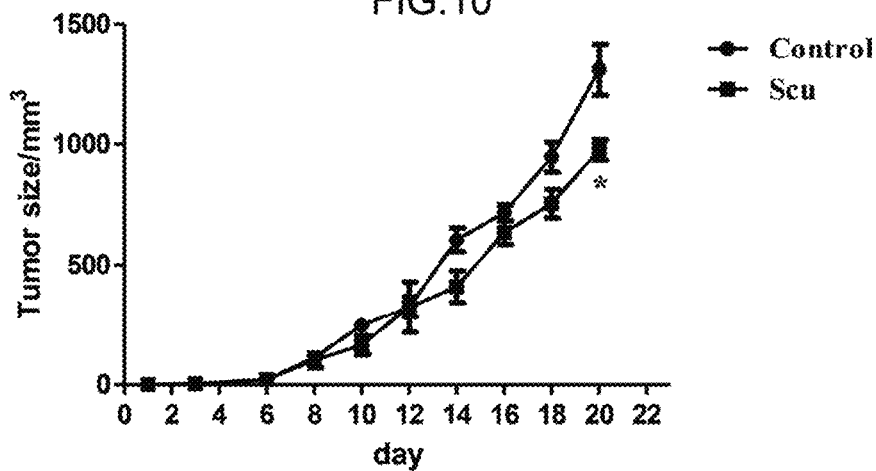
FIG. 11 shows inhibition of tumor growth in a mouse 4T1 tumor model by scutellarin. Balb/c mice were injected subcutaneously with 4T1 cells, and were injected with scutellarin (50 mg/kg/day) when the tumor grew to about 5 mm. On day 20 after tumor inoculation, scutellarin could significantly inhibit the tumor size.

Based on the previous results, we explore whether scutellarin has an anti-tumor effect. BALB/c mice were injected subcutaneously with 4T1 cells, and were injected intraperitoneally with scutellarin (50 mg/kg/day) when the tumor grew to about 5 mm. The tumor volume of the mouse was measured daily, and the volume was calculated by a formula: volume=length×width$^2$÷2. The tumor volume of the scutellarin treatment group was compared with the tumor volume of the untreated group. The results showed that scutellarin could significantly inhibit the tumor size on day 20 after tumor inoculation (FIG. 11).

As can be seen from the above results, WEHI-13VAR provides a bioassay for detecting TNF with specificity, stability and sensitivity. Actinomycin D (AcD) is an agent widely used in TNF bioassays to increase cytotoxicity of TNF. In the presence of AcD, WEHI-13VAR is extremely sensitive to TNF-induced cell death. The results show that TNF and WEHI-13VAR cells can be considered as a stable screening system, which is firstly used by us for the screening of TNFR2 antagonists, and it can be confirmed that the CHIs or compounds screened out have inhibitory effect on the expression of TNFR2, the proportion of TNFR2$^+$Foxp3$^+$ Tregs and the proliferation of Tregs. Therefore, this TNF bioassay and the WEHI-13VAR cell system can be used as an effective and stable system for screening TNFR2 modulators.

CHIs have been developed in China and used to treat some diseases including hypertension, nephrotic syndrome, coronary artery disease, rheumatoid arthritis, fracture, diabetes, and cervical neurodegenerative diseases. These new CHIs have changed the traditional administration mode, whereas the characteristics of traditional Chinese medicine are still retained. Scutellarin is a flavonoid compound isolated from *Erigeron breviscapus* (vant) Hand-Mazz and is a main component of DZXX officially listed in the Chinese Pharmacopoeia. In recent years, the mechanistic study of scutellarin has made a great progress in the treatment of various diseases, including cardiovascular and cerebrovascular diseases, neurodegenerative diseases, inflammation, cancer, and so on. The results of the present disclosure show that the screened CHIs and scutellarin have an inhibitory effect on TNF-induced cell death and have no effect on AcD-induced cell death. Moreover, CHIs can inhibit the expression of TNFR2 and the number of Tregs in an in vitro experiment, while scutellarin has an inhibitory effect on Tregs in both in vivo and in vitro experiments.

CD4$^+$Foxp3$^+$Tregs cells are potent immunosuppressive cells that play indispensable roles in maintaining homeostasis and inhibiting autoimmune responses. However, it can also promote the invasion and escape of tumor cells. As a pleiotropic cytokine, TNF can stimulate the proliferation of Tregs via the TNF-TNFR2 interaction, and the expression of TNFR2 is related to the enhancement of Tregs stability and inhibitory function. Although thalidomide is identified as the first TNFR2 inhibitor, recent studies have mainly focused on TNFR2-targeting biologics, which have relatively high targeting specificity and binding potency to receptors. However, it may be difficult to block the TNF-TNFR interaction by small molecule compounds due to the relatively large contact area of TNFR2. Studies have shown that TNFR2 has three major signaling pathways in T lymphocytes, including IKK/NFκB, MAPK (Erk1/2, p38, JNK), and PI3K/Akt signaling pathways. Therefore, it is meaningful to investigate the effect of targeted small molecule inhibitors that target the major components of the Tregs signaling pathways and thereby modulate Tregs activity.

In recent years, the mechanism study of scutellarin has made a great progress in the treatment of various diseases. It has been reported that long-term administration of scutellarin in a rat model with chronic myocardial infarction can inhibit cardiac fibroblast proliferation and collagen generation, whose mechanism includes inhibition of p38 MAPK and ERK1/2 phosphorylation. In a mouse model with LPS-induced acute lung injury, scutellarin (50 mg/kg) can significantly down-regulate LPS-induced TNF level. LPS-induced TNF can stimulate the proliferation of Tregs. Our research results show that scutellarin at this dose has an inhibitory effect on the amount of Tregs and significantly inhibits the expression of TNFR2. This mechanism may be to inhibit the proliferation of Tregs by inhibiting TNF-TNFR2 interaction. Moreover, scutellarin is a potent inhibitor against NF-κB activation and nuclear translocation, wherein NF-κB helps to inhibit the expression of matrix metalloproteinases (MMP-2, -9, and -14), thereby promoting tumor metastasis. Therefore, it is meaningful to investigate whether scutellarin exerts anti-tumor effects by inhibiting tumor-infiltrating regulatory T cells through inhibition of TNFR2 or TNFR2-related signaling pathways.

In addition to being expressed on suppressive Tregs cells, TNFR2 is also expressed on CD4$^+$Foxp3$^-$Teffs cells stimulated by TCR. Although the expression of TNFR2 is much lower in Teffs than in Tregs, the use of TNFR2-targeting drugs should be carefully evaluated. In addition, TNFR2 is also expressed on other types of cells, including endothelial cells, microglia, and specific nerve cell subtypes, cardiomyocytes, oligodendrocytes, myeloid-derived suppressor cells, and mesenchymal stem cells. TNFR2-targeting agents such as scutellarin may regulate physiological characteristics such as proliferation, death or activity of these cells by acting on TNFR2.

In addition to TNFα, there is a cytotoxin named lymphotoxin (LNα), which is mainly produced by activated T lymphocytes and is functionally similar to TNF. Sensitivity to cytotoxicity is significantly increased, when TNF/LN is present in sensitive cells such as L-929, LM and WEHI-13var and one or more metabolic inhibitors such as actinomycin D, mitomycin C or emetine are added. These inhibitors mainly function as transcriptase blockers, among which AcD is the most commonly used. Our results show that WEHI-13VAR is extremely sensitive to TNF-induced cell death in the presence of AcD, and its cytotoxicity is mediated by TNFR2, as cell survival increases after TNFR2 is blocked. Moreover, the screened CHIs and scutellarin are unable to inhibit AcD-induced cell death, which provides more evidence for their action on TNF-TNFR2. Since LNα homologs can also bind to TNFR2, it is interesting to investigate whether scutellarin can inhibit LNα-induced cytotoxicity to WEHI-13VAR and proliferation of Tregs by inhibiting LNα-TNFR2.

Finally, our research clearly shows that WEHI-13VAR and TNF can be considered as a stable screening system that can be used for screening pharmaceutical agents targeting TNFR2. Moreover, scutellarin can inhibit TNF-induced proliferation of Tregs, and expression of TNFR2 and Foxp3 on Tregs. Tumor-infiltrating Tregs, as immunosuppressive cells, facilitate growth and escape of tumor, thus scutellarin which inhibits the proliferation of Tregs by blocking the TNF-TNFR2 interaction can be further applied to the research on cancer immunotherapy and treatment of other diseases.

Materials and methods involved in the above embodiments are as follows.

(1) Mice and reagents

Wild type (WT) C57BL/6J (8-12 weeks old) female mice were provided by the Animal Facility of University of Macau. The animal research program was approved by the Animal Research Ethics Committee of University of Macau. RPMI-1640 (1×), fetal bovine serum (FBS), trypsin-EDTA (0.25%) phosphate buffered saline (1×), Pen Step, HEPES (1 M) and trypan blue (0.4%) were purchased from Thermo Fisher Scientific (United States). Antibodies were purchased from BD Pharmingen (San Diego, Calif.) and consisted of PerCP-Cy5.5 anti-mouse CD3 (145-2C11), FITC anti-mouse CD3 (145-2C11), FITC anti-mouse TCRβ (H57-597), PE anti-mouse CD120b/TNFR2 (TR75-89), and PerCP-Cy5.5 anti-mouse CD4 (RM4-5). Antibodies purchased from eBioscience include PE-Cy7 anti-mouse CD4 (GK1.5) and APC anti-mouse/rat Foxp3 staining set (FJK-16s). Recombinant mouse IL-2 and TNF were purchased from BD Pharmingen. LPS from Salmonella (Cat #: L9764) were purchased from Sigma-Aldrich. All Chinese herbal injections were purchased from hospitals in Zhuhai and Shanghai (China). Scutellarin (purity≥98%) was purchased from Chengdu Must Bio-technology Co., Ltd (China). MTT and dimethyl sulfoxide (DMSO) were obtained from Sigma-Aldrich (St. Louis, Mo., USA).

(2) Cell line and cell culture

WEHI-13VAR and 4T1 cells were purchased from American Type Culture Collection (Manassas, USA). WEHI-13VAR cells were cultured in RPMI-1640 containing 10% FBS, 1% L-glutamine, 1% HEPES and 1% Pen step. 4T1 cells were cultured in RPMI-1640 containing 10% FBS, 1% L-glutamine and 1% Pen step. The cell incubator was maintained at 5% $CO_2$ concentration and at a temperature of 37° C.

(3) TNF bioassay

WEHI-13VAR cells were seeded in 96-well plates at $1.5 \times 10^4$ cells/well. After incubation overnight, 2-fold diluted TNF with or without other CHIs or scutellarin was dissolved in RPMI-1640 medium containing 25 mM HEPES, 3% FBS and 0.5 μg/ml AcD at final concentration. Only medium was used in the control group. After culture for 18-20 hours, 10 μL of MTT (5 mg/mL) was added to each well and incubated for 4 hours in darkness. After the incubation, the medium was removed, and then 100 μL of DMSO was added to each well to dissolve the formazan blue crystals. Absorbance values were read at 570 nm using a 1420 Multilabel counter victor (PerkinElmer, Waltham, Mass., USA). Cell viability was expressed as the ratio of absorbance values between the sample and the blank control group.

(4) Cell purification and in vitro cell culture

Lymphocytes were obtained from spleens, axillary lymph nodes, inguinal lymph nodes and mesenteric lymph nodes of mice. CD4+ T cells were purified from lymphocytes by using CD4 (L3T4) microbeads (Miltenyi Biotec, 130-097-145) and MS columns (Miltenyi Biotec). MACS-purified CD4+ cells were labeled with CFSE, and the cells ($5 \times 10^4$ cells/well) were cultured in 96-well plates, and then stimulated with IL-2 or IL-2 plus TNF in the presence or absence of DZXX (20 μl/ml) for 3 days. The proliferation of Tregs was assessed by CFSE dilution assay, and the proportion of Foxp3+ cells in the CD4+ subset and the proportion of TNFR2 expressed on Tregs were analyzed by FACS. In other experiments, lymphocytes were stimulated with IL-2 or IL-2 plus TNF in the presence or absence of scutellarin (25-50 μM). The expression of Foxp3 and TNFR2 was analyzed by FACS.

(5) In vivo administration of LPS and scutellarin

Wild type C57BL/6J mice were intraperitoneally injected with 0.2 mL of saline or 200 μg of LPS. The mice in the administration group were treated with scutellarin (25 mg/kg or 50 mg/kg) immediately after being treated with LPS. Scutellarin was dissolved in saline. After 24 hours, the mice were sacrificed. Spleens, and lymph nodes at axillary, inguinal and mesenteric regions were collected for FACS analysis.

(6) Flow cytometry

After FcR was blocked, the cells were incubated with appropriately diluted antibodies and finally suspended in FACS buffer for subsequent analysis. Experimental data acquisition was performed by BD FACSCanto II and BD FACSAria™ Fusion flow cytometer. Data analysis was performed using FlowJo software (Tree Star Inc., Ashland, Oreg.).

(7) Statistical analysis

The mean±standard deviation (SD) was determined for each group. Statistical analysis was performed using one-way analysis of variance (one-way ANOVA) and Tukey's test, or two-way analysis of variance (two-way ANOVA). The difference was considered to be statistically significant when $p<0.05$, and the exact p value was shown unless $p<0.001$. The concentration dependence was visually determined from the graphs. All statistical analyses were performed with GraphPad Prism 7.0.

(8) This project involved in the present disclosure was funded by Macau Science and Technology Development Fund (FDCT) research grant 014/2015/A1 and 201/2017/A3, and University of Macau research grant MYRG2016-00023-ICMS-QRCM and MYRG2017-00120-ICMS.

The above-described examples are merely the preferred examples of the present disclosure, and are not intended to limit the present disclosure. For those skilled in the art, various changes and variations are encompassed in the present disclosure. Any modifications, equivalent substitutions, improvements, and so on made within the spirit and principle of the present disclosure are intended to be included within the scope of the present disclosure.

What is claimed is:

1. A method for modulation of proliferation or death of cells, comprising allowing the cells to contact with scutellarin or a pharmaceutically acceptable salt thereof,
   wherein the cells are WEHI-13VAR cells that express TNFR2, and the proliferation or death of the cells is caused or mediated by interaction between TNF and TNFR2.

2. The method according to claim 1, wherein the modulation of proliferation or death of cells comprises inhibition of proliferation or death of cells.

3. The method according to claim 1, wherein the scutellarin inhibits proliferation or death of cells by blocking the interaction between TNF and TNFR2.

* * * * *